(12) United States Patent
Feinsod

(10) Patent No.: US 6,514,223 B1
(45) Date of Patent: Feb. 4, 2003

(54) WICKING INSTRUMENT FOR LASIK SURGERY

(76) Inventor: Matthew Feinsod, 4F Nassau Dr., Great Neck, NY (US) 11021

( * ) Notice: Subject to any disclaimer, the term of this patent is extended or adjusted under 35 U.S.C. 154(b) by 0 days.

(21) Appl. No.: 09/419,130

(22) Filed: Oct. 15, 1999

(51) Int. Cl.[7] .................. A61M 35/00; A61F 11/00; A47K 7/02
(52) U.S. Cl. .................. 604/1; 604/294; 15/244.4; 606/162
(58) Field of Search .................. 604/1–3, 294; 15/244.1, 244.4; 606/162

(56) References Cited

U.S. PATENT DOCUMENTS

| | | | | |
|---|---|---|---|---|
| 355,308 A | * | 1/1887 | Foote | 604/1 |
| 1,629,436 A | * | 5/1927 | Capri | 604/1 |
| 2,510,961 A | * | 6/1950 | Davis | 604/1 |
| 4,883,454 A | * | 11/1989 | Hamburg | 604/1 |
| 5,044,040 A | * | 9/1991 | Tetrault | 604/1 |
| 5,676,643 A | * | 10/1997 | Cann et al. | 604/1 |
| 5,700,239 A | * | 12/1997 | Yoon | 604/2 |
| 5,738,643 A | * | 4/1998 | Stredic, III | 604/1 |

* cited by examiner

*Primary Examiner*—Dennis Ruhl
(74) *Attorney, Agent, or Firm*—Frommer, Lawrence & Haug LLP; William S. Frommer; Gordon Kessler

(57) ABSTRACT

An apparatus and method are provided for use in removing liquid from under a corneal flap generated during LASIK surgery. The apparatus comprises a handle, a sickle-shaped end coupled to the handle, the sickle-shaped end having a concave and a convex portion, and a sponge coupled with the concave portion of the sickle-shaped end, extending along the convex portion thereof, and being shaped substantially similarly to the sickle-shaped end. The sickle-shaped end extends from approximately 180° to 270°, or any other desired part of a circle and may have sponge on one or both sides thereof. The radius of the sickle-shaped end is the same or slightly larger than the diameter of a corneal flap generated during LASIK surgery so that when the apparatus is placed adjacent the cornea of a patient about the corneal flap, liquid is wicked from thereunder without requiring any contact with the corneal flap.

2 Claims, 5 Drawing Sheets

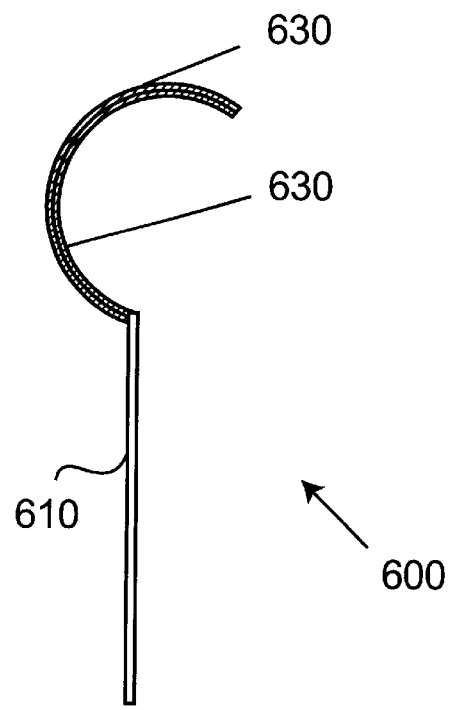
FIG. 6
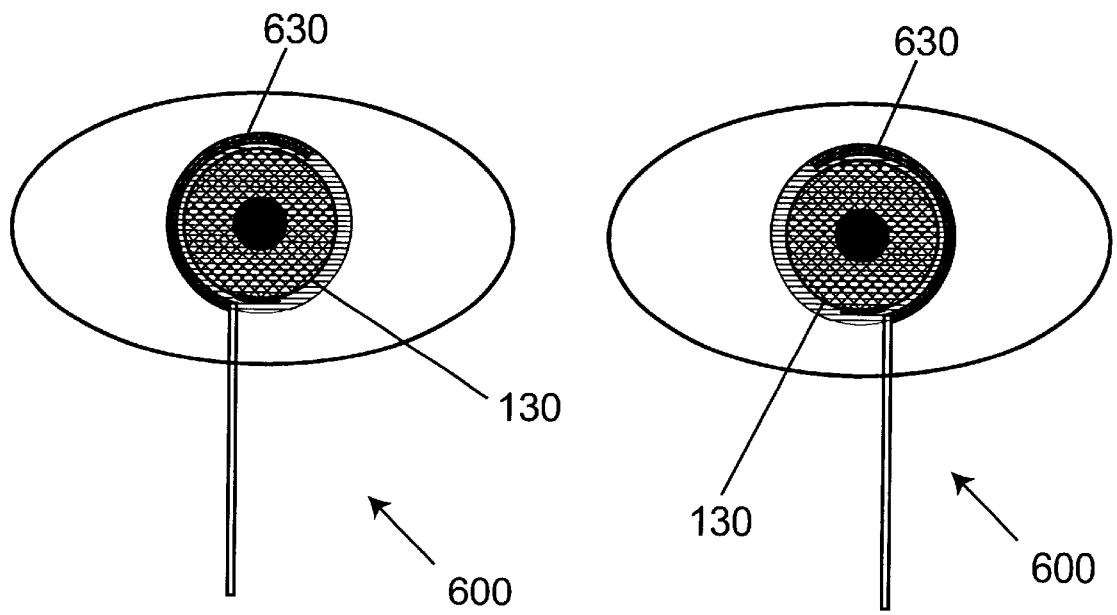
FIG. 7A  FIG. 7B

WICKING INSTRUMENT FOR LASIK SURGERY

BACKGROUND OF THE INVENTION

Refractive eye surgery is a general term for a surgical procedure intended to improve or correct the focus of a patient's eyes by changing the shape of the eye, thereby changing the optics by which the eye sees various images. While surgeries reshaping various portions of a patient's eye have been employed for some time, most recently, refractive eye surgery has involved reshaping the cornea of a patient's eye.

The cornea is the clear, front surface of the eye of a person which refracts, or bends light as it enters the eye. This light that is bent by the cornea is focused on the retina of the eye. The retina is a layer of light-sensitive cells that lines the back of the eye. The retina converts light rays incident thereon into electrical impulses. These electrical impulses are sent through the optic nerve of the person to his or her brain. In the brain, these impulses are interpreted as images. If images received by the eye and refracted or bent by the cornea are not properly focused on the retina, the eye is said to have a refractive error. Myopia (near-sightedness), hyperopia (far-sightedness), and astigmatism (distortion at both near and far distances) are terms used to describe the refractive error of an eye. These refractive errors are the result of various irregular corneal curvatures, lens curvatures, or axial eye lengths that prevent images from being focused to a single point on the eye's retina.

In performing refractive eye surgery, an excimer laser (excited dimer) may be used to reshape the cornea, thereby enabling the cornea to properly focus received light on the retina. The excimer laser interacts with the corneal tissue of the eye utilizing a laser-tissue interaction called photoablation. In photoablation, ultraviolet laser pulses precisely etch the cornea by uncoupling various intermolecular bonds thereof, thereby removing a submicron layer of cornea under highly controlled conditions. Because there is a relative absence of thermal injury to the corneal tissue during this procedure, the corneal cells can be ablated without opacifying (rendering so that light cannot pass therethrough) adjacent tissue. Such opacification might result in the inability to see through the opacified tissue of the eye. By carefully controlling the number of pulses of the ultraviolet laser, and the diameter and location of each pulse, the corneal tissue of a patient can be resculpted as necessary in order to improve the patient's vision.

An early procedure using such an excimer laser is called PRK (photorefractive keratectomy). In this procedure, the outer surface of a patient's eye is acted upon by the laser to change the shape of the cornea. While this procedure has been quite effective in improving a patient's vision, the procedure has a number of disadvantages. These include a relatively long recovery time after the procedure, discomfort for the patient during and after the procedure, possible infection of the eye after procedure, the requirement for a rigid post-operative regimen, and a limit in the type of refractive corrections that can be performed.

In an attempt to improve on the PRK procedure, a new procedure entitled LASIK, or laser-assisted in-situ keratomileusis has been developed utilizing the excimer laser for refractive surgery. This variation of the original PRK procedure has become widely accepted and is practiced by ophthalmologists worldwide. This procedure has a number of advantages over traditional PRK, including a faster recovery time, less discomfort for the patient, a lower risk of infection, a more convenient post-operative regimen, and the greatest range of refractive correction possibilities. As a result, the LASIK procedure has surpassed PRK in the number of annual procedures performed.

The LASIK procedure involves the use of the above-noted excimer laser for resculpting corneal tissue within the body of the cornea, known as the corneal stromal bed, as opposed to resculpting the surface and stroma of the cornea, as performed in the PRK procedure. In LASIK, unlike PRK, a corneal flap is created by slicing the cornea along its lamnellar plane with an instrument called a microkeratome. The flap formed by this slicing, the outermost 20 percent of the thickness of the cornea, is lifted and reflected to the side. A connecting portion, or hinge between the flap and the eye remains so that the flap does not become completely disconnected from the remainder of the cornea. The reflecting of this flap serves to expose the corneal stroma, or middle layer of the corneal anatomy, to the computer-controlled laser pulses which reshape the corneal curvature. The excimer laser then reshapes the middle layer of the cornea.

After the corneal stromal bed is acted upon by the excimer laser, the flap is placed back in its original position on the cornea. The replacement of the flap provides coverage and protection for the internal surface of the cornea acted upon by the excimer laser. After the flap has been replaced, a steady stream of fluid is introduced under the flap, thereby momentarily "floating" the flap relative to the remainder of the cornea to eliminate any small amounts of debris that may be present between the flap and the remainder of the cornea as a result of the LASIK procedure. After a sufficient amount of fluid has been introduced, a milking or "squeegee" procedure follows for removing this excess fluid from beneath the flap margins, or "gutters". Finally, the flap gutters are further dried so as to seal and adhere the corneal flap to the remainder of the cornea. This drying is conventionally performed by applying merocel (PVA) sponge spears, one point at a time, to various positions around the circumferential edge of the corneal flap.

After the LASIK procedure, many patients' vision returns to an uncorrected 20/20, and occasionally even better with excellent visual improvement over the first 24 hours. Occasionally, results are less impressive than expected. If there is no debris in the flap-stroma interface, and no intralamellar microfolds or wrinkles (striae) in the flap, the likelihood for an excellent result increases dramatically. Thus, a pristine initial postoperative appearance typically leads to faster visual recovery, better visual results, and a decreased chance of significant inflammatory reaction. However, the introduction of any debris or striae under or in the flap will require the flap to be lifted a second time to avoid inflammation of the eye, generation of an irregular astigmatism, or any other compromised results. The degree of flap manipulation, or the number of times the flap must be touched, moved or contacted is directly related to the generation of flap striae. Thus, the less the flap needs to be touched, the less the chance of striae being generated.

A critical step in the procedure, and a step which if performed properly greatly reduces the occurrence of striae, involves the replacement of the flap and subsequent flap and corneal stroma irrigation, drying of the space between the flap and the corneal stroma and adhesion of the flap to the corneal stroma bed. As noted above, after completion of the LASIK laser treatment, surgeons advocate irrigating between the flap and the corneal stromal bed very thoroughly at the flap-stroma interface to eliminate any debris therefrom. The introduction of this irrigating solution creates a lake of fluid, as noted above, floating the flap momentarily, so that any debris is removed therefrom. This fluid and the hinge remaining between the flap and the corneal stroma bed also guides the flap back into proper position. After being properly replaced, as also noted above, the next step in the procedure involves removing the liquid from the interface between the flap and the stroma of the cornea. This process is performed by milking or squeegeeing of this fluid with a moist merocel (PVA) sponge over the surface or epithelium of the cornea and corneal flap. A sponge is placed in the middle of the cornea, and is passed over the corneal flap to the outer surface thereof to force the liquid from beneath the flap. This process is performed a plurality of times as necessary to remove fluid from beneath the flap. Other variations which perform a similar function of applying pressure to the flap surface to remove fluid from under the flap include the use of a flap applanator or the use of a corneal compressor, as is well-known in the art.

However, it is this step involving contact with the surface of the flap that is fraught with danger. First, any of the sponges or instruments that are dragged across the corneal epithelium may create a corneal abrasion, and sometimes may even puncture the corneal epithelium entirely. The result of such an abrasion or puncture of the cornea is painful, and the eye may be prone to infection. Additionally, such an abrasion can produce unpredictable visual outcomes which are less successful than desired. In addition, whether a sponge or other instruments are used in this procedure, the milking process involves depressing the delicate corneal flap, dramatically increasing the chances of generating striae therein, or other problems with the flap, thereby further adversely affecting refractive outcome.

After the milking or squeegee process has been completed, further drying is typically required circumferentially around the flap margins to encourage adhesion of the flap to the underlying stroma of the cornea. This is customarily achieved by gently applying a dry merocel sponge spear one point at a time to the entire approximately 270° margin circumference, thereby wicking any residual fluid therefrom. This is a time-consuming, tedious process that involves multiple touches to the flap margin to remove the fluid therefrom. Because of these multiple touches to the flap, damage around the edge surface thereof, or the generation of striae therein are possible. Furthermore, the flap may shift out of alignment before adhesion as a result of these touches, once again reducing the success of the refractive outcome of the surgery. Therefore, it would be beneficial to provide a method and apparatus for removing excess liquid from under the corneal flap, while reducing the required level of manipulation of the corneal flap and direct contact with the corneal flap.

OBJECTS OF THE INVENTION

It is therefore an object of the invention to provide an improved method and apparatus for wicking fluid from underneath a corneal flap during the performance of a LASIK surgery procedure.

Another object of the invention is to provide an improved liquid wicking method and apparatus that removes excess liquid from under a corneal flap after LASIK surgery has been performed without coming into direct contact with the corneal flap, and without moving the corneal flap.

A further object of the invention is to provide an improved method and apparatus for insuring proper adhesion between a corneal flap and the remainder of the corneal stroma bed after LASIK surgery has been performed by removal of liquid from under the corneal flap until the interface between the corneal flap and the remainder of the cornea is dry, without making contact with the corneal flap.

Still other objects and advantages of the invention will in part be obvious and will in part be apparent from the specifications and the drawings.

SUMMARY OF THE INVENTION

A method and apparatus, in accordance with the invention for removing liquid from under a corneal flap replaced after LASIK surgery, is provided that allows for the removal of this liquid without contact between the instrument and the corneal flap. In a first embodiment, the instrument comprises a handle with a sickle-shaped end forming approximately 270° of a circle. One face of the sickle-shaped end of the instrument has a merocel PVA sponge attached thereto and conforming to the shape of the 270° sickle-shaped end of the instrument. During use, the diameter of sickle-shaped end of the instrument is provided to be the same or slightly larger than the typical circumference of a corneal flap produced during LASIK surgery. A handle thereof may be provided at any desired angle to the plane of the sickle-shaped end of the instrument to aid in the manipulation thereof.

After surgery, the sickle-shaped end of the instrument, including the merocel sponge, is placed adjacent to the cornea of a patient to form a 270° crescent just slightly larger than outside circumference of the corneal flap. By capillary action, liquid from under the corneal flap is drawn into the merocel sponge. In this manner, liquid can be removed from under the corneal flap without contacting the corneal flap, thereby improving results of LASIK surgery.

In an alternative embodiment, rather than having the sponge merely conform to the sickle-shaped portion of the instrument, extended portions of the sponge material are provided to extend across a user's conjunctiva to allow for the removal of excess liquid. More liquid may be removed and held by the apparatus of this alternative embodiment so that only one instrument need be used for each eye.

In a further alternative embodiment, rather than including a 270° sickle-shaped end, the instrument of this embodiment includes a semi-circular end of approximately 180°, and is provided with a merocel sponge on either side of the semi-circular instrument substantially parallel to the plane thereof. Thus, the sponge on one side of the semi-circular end of the instrument can be used for removing liquid from under one side of the corneal flap, and thereafter the instrument can be flipped over and the sponge on the other side of the semi-circular end of the instrument can be used to remove liquid from the other side of the corneal flap.

The invention accordingly comprises the several steps and the relation of one or more of such steps with respect to each of the others, and the apparatus embodying features of construction, combinations of elements, and arrangements of parts that are adapted to effect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which:

FIG. 6 depicts a wicking instrument constructed in accordance with a third embodiment of the invention;

FIGS. 7A and 7B depict the wicking instrument of FIG. 6 in use on opposite sides of a corneal flap.

DETAILED DESCRIPTION OF THE PREFERRED EMBODIMENTS

Figure 1:
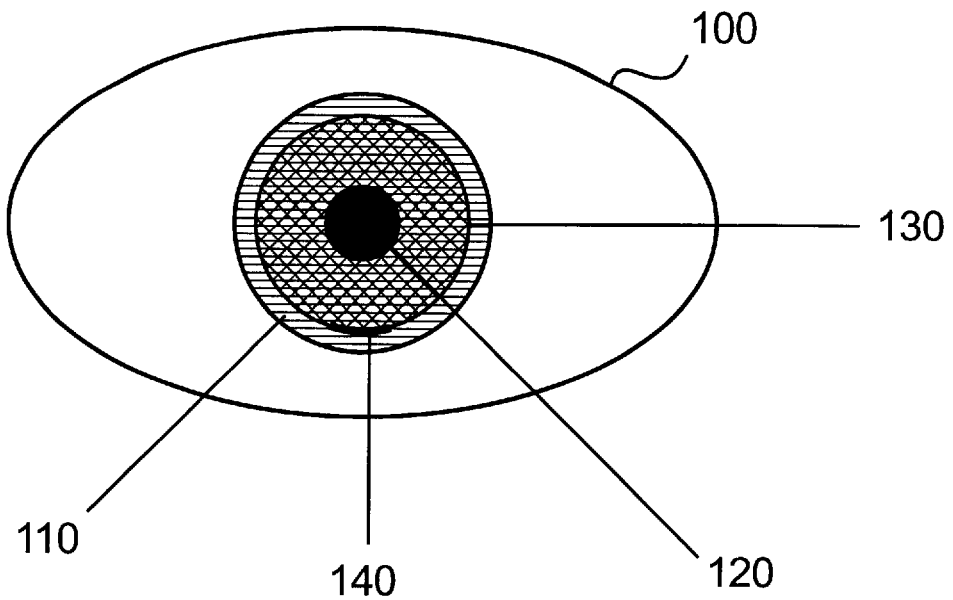
FIG. 1 depicts an eye, along with a corneal flap and a corneal flap margin.

Referring first to FIG. 1, a corneal flap generated through the performance of LASIK surgery procedure is depicted in reference to a patient's eye. A patient's eye is shown at 100 and a colored iris portion thereof is shown at 110. 120 depicts the patient's pupil. A corneal flap margin 130 about a corneal flap 150 is depicted as an almost complete circle extending just inside most of the iris colored portion 110 except for a hinged portion 140. This corneal flap margin is generated during LASIK surgery, and hinged portion 140 maintains the corneal flap portion in contact with the corneal stroma of the cornea 110. As noted in the Background and Summary of the Invention, after performance of LASIK surgery, this area underneath corneal flap 150 and above the corneal stroma of cornea 110 is irrigated with a large amount of fluid to remove any debris therefrom and for floating the corneal flap so that it may be properly placed by hinged portion 140.

Figure 2:
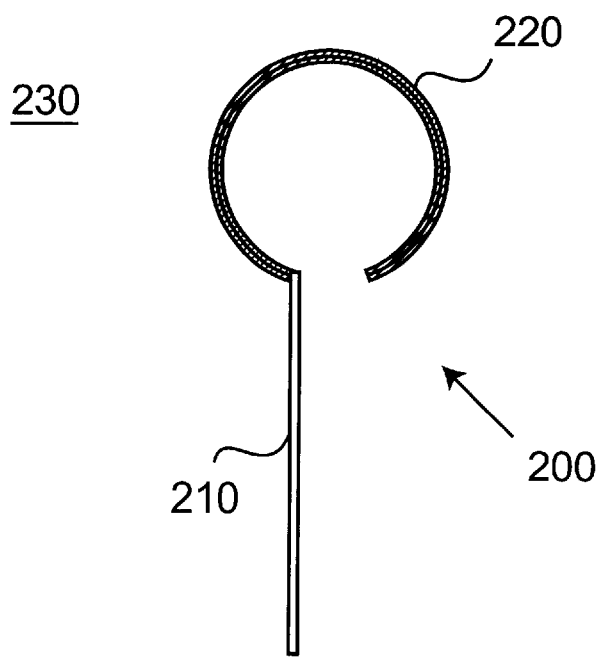
FIG. 2 depicts a wicking instrument constructed in accordance with a first embodiment of the invention.
Figure 8:
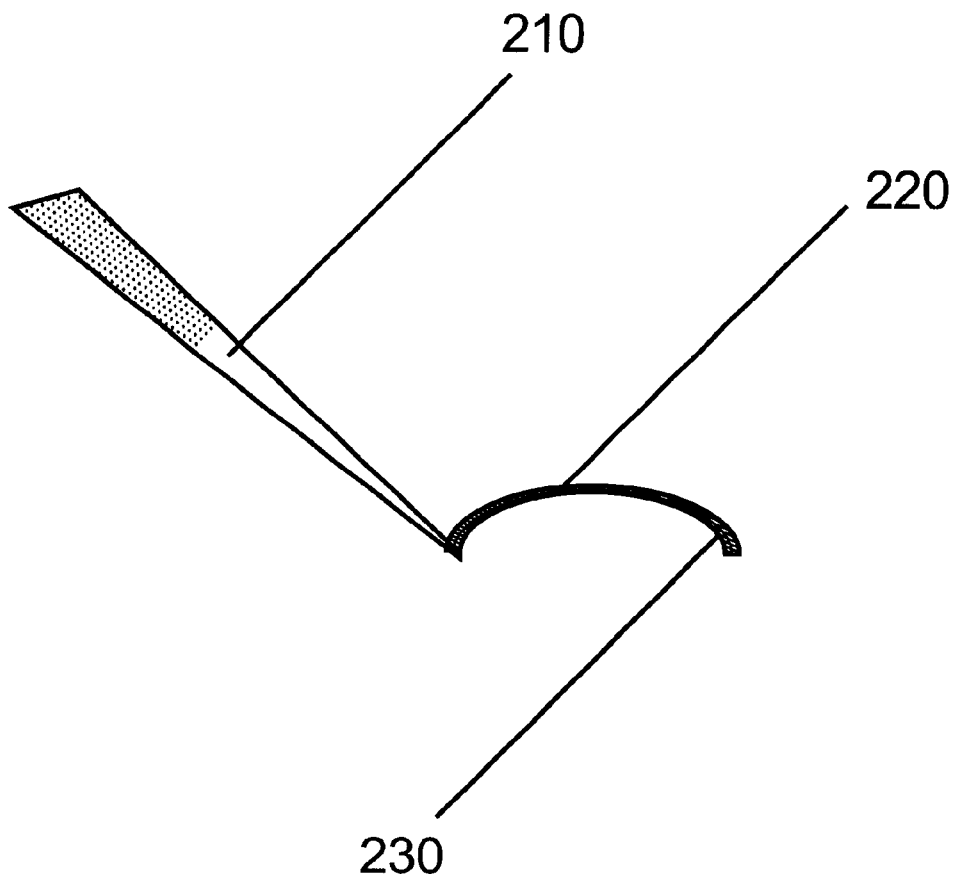
FIG. 8 depicts a wicking instrument constructed in accordance with an alternative embodiment of the invention.

Referring next to FIG. 2, an apparatus constructed in accordance with a first embodiment of the invention is depicted, indicated generally at 200. Wicking instrument 200 includes a handle portion 210, a sickle-shaped portion 220, and a highly absorbent PVA sponge portion 230 positioned coextensive with, and coupled to sickle-shaped portion 220. Handle or shaft 210 of the instrument is preferably formed with a rounded cross-section, and includes a coarse surface at the terminal end thereof opposite end 220 to improve grip of the instrument. While in FIG. 2 the handle is shown coplanar to the shape of sickle-shaped end 220, as is shown in FIG. 8, in an alternative construction it is also possible to position the shaft and handle portion 210 of the instrument at a 45° angle to the plane of the sickle-shaped end 220, or at any other angle which may be beneficial for improving ease of use of the instrument. Additionally, this angled handle may be applied to any of the embodiments of the invention.

The radius of sickle-shaped portion 220 of the instrument is slightly larger or equal to the radius of corneal flap 150, taking into account the width of sponge portion 230 coupled with end 220. This size allows for the maintenance of maximum surface contact with cornea 110, but positions sponge portion 230 just outside or at corneal flap margin 130. The instrument is preferably constructed of an injected molded sterile plastic, insuring a lightweight, disposable and sterile product. Sponge portion 230 is preferably attached to the inside, or concave edge of sickle-shaped end 320 of wicking instrument 200, but may be attached in any manner. The sponge continues along one side of sickle-shaped end 220, coplanar thereto, and also can extend in a direction perpendicular to the plane of sickleshaped end 220 outside, and at the convex portion thereof, if desired. The sponge is preferably composed of a highly absorbent wicking material such as polyvinyl alcohol (PVA) angled to conform to the shape of the peripheral cornea for maximum surface contact with cornea 110 and corneal flap margin 130. However, any material having the features of being synthetic, biocompatible and fiber-free, thereby reducing the chance of eye infections, may be used. Materials such as PVA and the like are preferable to fibrous materials such as cotton gauze and cellulose in order to minimize the debris which might be trapped under the corneal flap. Additionally, the sponge must be soft enough in its dry state to provide some flexibility at its apex where corneal contact is initiated. This flexibility will decrease the likelihood of flap movement upon contact of the cornea with the sponge.

The portion of the sponge at the concave or inside portion of sickle-shaped end 220 of wicking instrument 200 is preferably formed slightly beveled or otherwise shaped, having approximately a 7.5° of curvature, in a preferred embodiment, so as to match the normal corneal profile and to maximize contact of the sponge with the cornea to remove the most fluid from the corneal flap margin. The sponge is also provided at a thickness so as to maximize the absorption of excess fluid from under the corneal flap.

Figure 3:
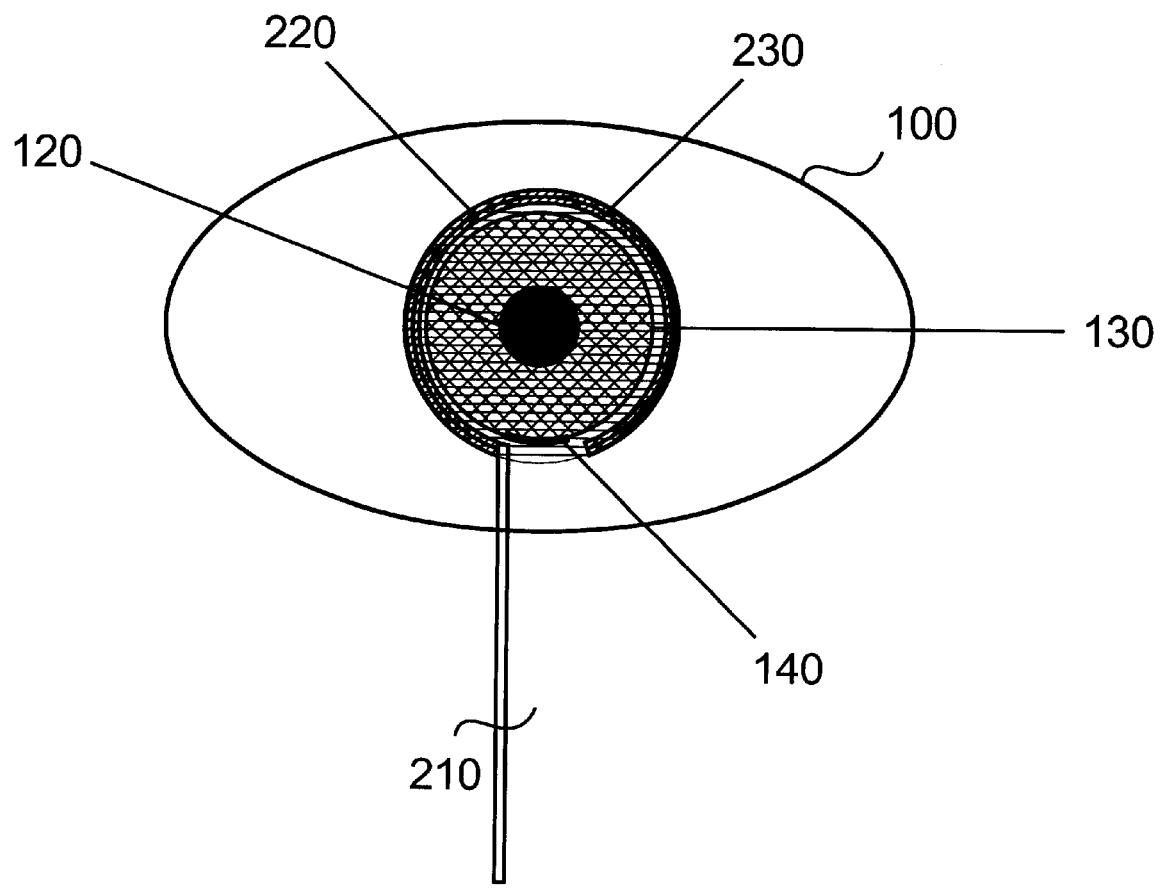
FIG. 3 depicts the wicking instrument of FIG. 2 in place around a corneal flap margin.

As is shown in FIG. 3, during use, wicking instrument 200 is placed so that sickle-shaped end 220 along with highly absorbent sponge 230 are positioned concentric with corneal flap margin 130 and as shown has a radius slightly larger than that of the corneal flap margin. The portion of sickle-shaped end 220 that is open (not the complete circle) is placed adjacent hinge 140 since it is not necessary to wick moisture therefrom. Upon placement, liquid is wicked from under the corneal flap into the sponge by capillary action. Through the use of this apparatus and method, it is therefore possible to wick liquid from under corneal flap 130 without making contact with the corneal flap, or squeegeeing or rolling, or risking other movement or abrasion of the corneal flap.

Figure 4:
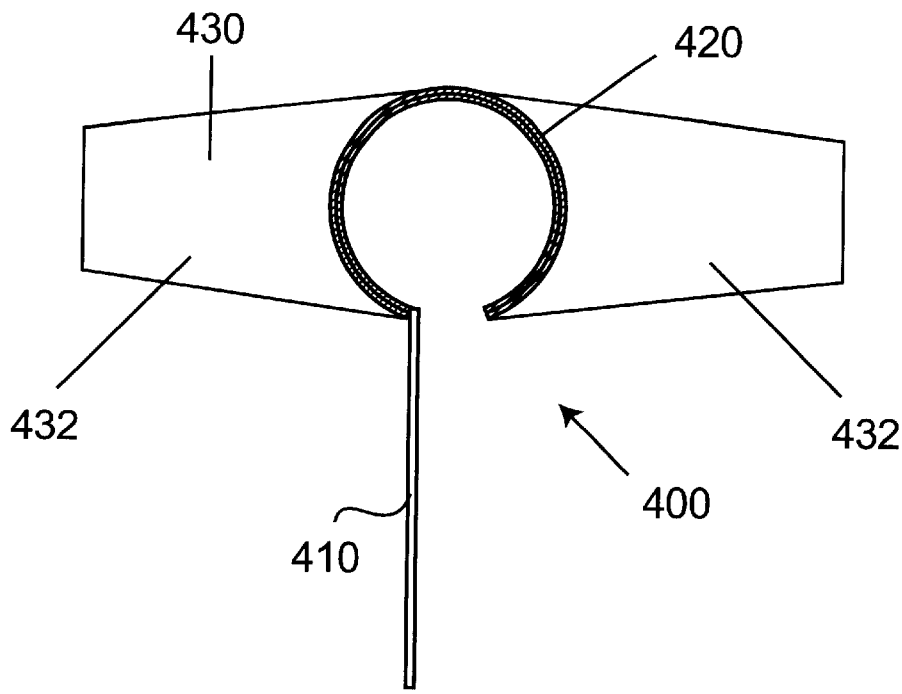
FIG. 4 depicts a wicking instrument constructed in accordance with a second embodiment of the invention.

Referring next to FIG. 4, a wicking instrument 400 constructed in accordance with a second embodiment of the invention is shown. Instrument 400 is provided with a handle 410, and a sickle-shaped end 420 similar to those of the first embodiment. A highly absorbent PVA sponge 430 is also provided, and within the concave or inner portion of sickle-shaped end 420 of instrument 400, is similarly shaped and situated to the sponge in the first embodiment. However, at the outside of concave portion of sickle-shaped end 420 of instrument 400, the sponge is provided with elongated portions 432 which conform generally in shape and size to a patient's eye. Thus, as noted above with respect to the first embodiment, while the portion of the sponge that is to touch a user's eye is beveled or otherwise shaped with curvature to match the normal corneal profile of the user's eye adjacent the corneal flap, portions 432 of sponge 430 are similarly contoured and curved to further match the curve of a patient's eye. These elongated portions 432 greatly increase the liquid-absorbing ability of the instrument.

Figure 5:
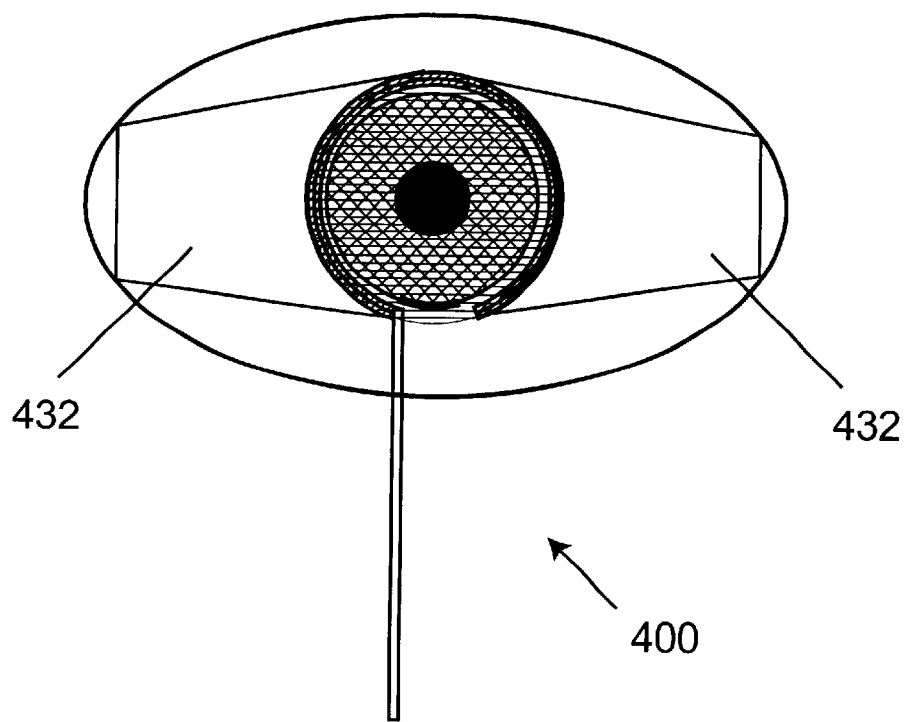
FIG. 5 depicts the wicking instrument of FIG. 4 in position around a corneal flap.

Referring to FIG. 5, during use instrument 400 is positioned similarly to instrument 200 of FIG. 3. Thus, the description of FIG. 3 is equally applicable to FIG. 5. The only difference being that elongated portions 432 allow for extra absorption surfaces for removing liquid from the patient's eye, insuring that only one instrument need be used for each procedure.

Referring next to FIG. 6, a wicking instrument, indicated generally at 600, constructed in accordance with a third embodiment of the invention is shown. In this embodiment, wicking instrument 600 is formed with a handle portion 610, a semi-circular shaped end 620 with a semi-circular shaped sponge 630 coupled therewith. Rather than the sponge only being provided on one surface of the instrument coplanar to the end, as is shown in FIGS. 2 and 4, in this third embodiment, sponge 630 is provided on both the upper and lower surfaces of the semi-circular shaped end 620, and coplanar therewith. Thus, as is shown in FIG. 7A, during use semi-circular end 620 of instrument 600 including sponge 630 is first placed adjacent the corneal flap margin so that sponge 630 wicks moisture from one side of the corneal flap margin. Thereafter, as is shown in FIG. 7B, semi-circular end 620 is flipped over and is placed so that sponge 630 is positioned adjacent the opposite side of corneal flap margin 130 from that of FIG. 7A. In this manner, both sides of the instrument are used in order to wick fluid from under opposite sides of corneal flap margin 130. The use of such a semi-circular shaped end may be beneficial if and when a corneal flap margin generated is of an irregular size or shape, allowing a user performing the wicking operation with slightly more latitude of movement.

Because this third embodiment must use both sides of the instrument, in the preferred embodiment, the handle is formed coplanar with the crescent-shaped instrument head, but may be provided with a slight angle, or a movable, changeable angle if desired.

In yet another alternative embodiment in the invention, it may be possible to construct the instrument of a light metal or other reusable material that may be sterilized. The sponge is removably attached thereto and is manufactured as a disposable attachment so that only the sponge portion need be replaced after each use.

In accordance with the invention, the uniquely shaped wicking instruments of the invention described above provide a number of benefits. First, the instruments allow the replacement of the risky squeegee step in the LASIK procedure, and also avoid the need to perform multiple wicking steps. Thus, flap adhesion can be improved by decreasing the amount of instrument-cornea contact. Therefore, in accordance with the invention, the currently used pushing or milking process of eliminating fluid from under the corneal flap is replaced with a gentle pulling or wicking mechanism which removes liquid by capillary action. The invention permits efficient, evenly distributed egress of fluid from under the corneal flap, thereby simultaneously serving to accomplish both the drying and adhesion steps. More importantly, the use of this method and apparatus significantly minimizes corneal flap manipulation and eliminates contact with the corneal flap surface entirely. As a result, the risk of the generation of corneal striae and abrasions are minimized accordingly. The use of this method apparatus of the invention will therefore lead to improved refractive outcomes, increased patient comfort, and healthier post-surgical corneas.

It will thus be seen that the objects set forth above, among those made apparent from the preceding description, are efficiently attained and, because certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method for wicking liquid from a corneal flap generated during LASIK surgery comprising the steps of:

providing a wicking instrument including a handle, a sickle-shaped end coupled to said handle, and a sponge coupled to said sickle-shaped end; and placing one side of said sickle-shaped end and said sponge coupled thereto adjacent to a corneal flap margin of said corneal flap, thereby wicking liquid from thereunder.

2. The method of claim 1, further comprising the steps of:

flipping said sickle-shaped end; and placing another side of said sickle-shaped end and said sponge coupled thereto adjacent to said corneal flap margin of said corneal flap.

\* \* \* \* \*